(12) United States Patent
Mukai et al.

(10) Patent No.: US 10,098,795 B2
(45) Date of Patent: Oct. 16, 2018

(54) ABSORBENT ARTICLE

(71) Applicant: Unicharm Corporation, Ehime (JP)

(72) Inventors: Hirotomo Mukai, Kagawa (JP); Takaya Arayama, Kagawa (JP)

(73) Assignee: Unicharm Corporation, Ehime (JP)

( * ) Notice: Subject to any disclaimer, the term of this patent is extended or adjusted under 35 U.S.C. 154(b) by 737 days.

(21) Appl. No.: 14/395,031

(22) PCT Filed: Apr. 19, 2013

(86) PCT No.: PCT/JP2013/061662
§ 371 (c)(1),
(2) Date: Oct. 16, 2014

(87) PCT Pub. No.: WO2013/161717
PCT Pub. Date: Oct. 31, 2013

(65) Prior Publication Data
US 2015/0073373 A1    Mar. 12, 2015

(30) Foreign Application Priority Data

Apr. 23, 2012  (JP) ................................ 2012-098253

(51) Int. Cl.
*A61F 13/49*  (2006.01)
*A61F 13/535*  (2006.01)
*A61F 13/494*  (2006.01)

(52) U.S. Cl.
CPC .. *A61F 13/49011* (2013.01); *A61F 13/49001* (2013.01); *A61F 13/49017* (2013.01);
(Continued)

(58) Field of Classification Search
CPC .......... A61F 13/49017; A61F 13/49019; A61F 13/49061; A61F 13/4906
See application file for complete search history.

(56) References Cited

U.S. PATENT DOCUMENTS

| 5,197,960 A | 3/1993 | Nomura et al. |
| 2001/0007936 A1 * | 7/2001 | Shimoe ............. A61F 13/49019 604/385.24 |

(Continued)

FOREIGN PATENT DOCUMENTS

| DE | 202011000820 U1 | 9/2011 |
| EP | 2 258 326 A1 | 12/2010 |

(Continued)

OTHER PUBLICATIONS

Chinese Office Action and English translation from corresponding Chinese application No. 201380021581.0 dated Mar. 28, 2016 (11 pgs).

(Continued)

*Primary Examiner* — Susan Su
(74) *Attorney, Agent, or Firm* — Brinks Gilson & Lione

(57) ABSTRACT

An absorbent article that has an exterior body. In the exterior body is an edge part which is forming a part of the leg opening unit. A rear end of the absorber is positioned in the crotch region so as not to overlap with a waistline elastic member. In an absorber disposition region in which the absorber is disposed, an end in a widthwise direction of the exterior body is positioned inside in the widthwise direction more significantly than an end in the widthwise direction of the absorber, and a part of a leg-holes elastic member is disposed.

12 Claims, 10 Drawing Sheets

(52) U.S. Cl.
CPC ...... *A61F 13/49406* (2013.01); *A61F 13/535* (2013.01); *A61F 2013/4948* (2013.01); *A61F 2013/5355* (2013.01)

(56) References Cited

U.S. PATENT DOCUMENTS

| | | | | |
|---|---|---|---|---|
| 2001/0016723 | A1* | 8/2001 | Sayama | A61F 13/49019 604/398 |
| 2001/0031957 | A1* | 10/2001 | Prestley | A61F 13/49 604/385.25 |
| 2002/0007172 | A1* | 1/2002 | Takei | A61F 13/15601 604/385.27 |
| 2002/0045872 | A1* | 4/2002 | Shimada | A61F 13/49011 604/385.3 |
| 2002/0045877 | A1* | 4/2002 | Shimada | A61F 13/49011 604/385.29 |
| 2002/0068919 | A1* | 6/2002 | Shinohara | A61F 13/49017 604/385.27 |
| 2002/0072728 | A1* | 6/2002 | Shinohara | A61F 13/49017 604/385.29 |
| 2002/0147438 | A1* | 10/2002 | Tanaka | A61F 13/496 604/392 |
| 2006/0161131 | A1* | 7/2006 | Kurata | A61F 13/15593 604/385.28 |
| 2007/0208317 | A1* | 9/2007 | Krautkramer | A61F 13/49019 604/385.3 |
| 2008/0114325 | A1* | 5/2008 | Edwall | A61F 13/49011 604/385.24 |
| 2012/0302985 | A1* | 11/2012 | Mukai | A61F 13/15593 604/385.24 |
| 2013/0102987 | A1* | 4/2013 | Mukai | A61F 13/49011 604/385.29 |
| 2014/0163509 | A1* | 6/2014 | Gassner | A61F 13/49061 604/385.16 |

FOREIGN PATENT DOCUMENTS

| | | |
|---|---|---|
| JP | 08-280739 | 10/1996 |
| JP | 2004-248769 A | 9/2004 |
| JP | 3957726 B2 | 8/2007 |
| JP | 2011-177310 A | 9/2011 |
| JP | 2011-206217 A | 10/2011 |
| WO | WO 2004/000188 A1 | 12/2003 |
| WO | WO 2011/105412 A1 | 9/2011 |

OTHER PUBLICATIONS

European Communication from corresponding European application No. 13 781 600.5 dated May 4, 2016 (4 pgs).
Chinese Office Action and English translation from corresponding Chinese application No. 201380021581.0 dated Jul. 31, 201513 (11 pgs).
International Search Report from corresponding PCT application No. PCT/JP2013/061662 dated Jun. 11, 2013 (2 pgs).
European extended Search Report from corresponding European application No. 13781600.5 dated Oct. 29, 2015 (7 pgs).
Japanese Office Action and English translation from corresponding Japanese application No. 2012-098253 dated Oct. 30, 2015 (6 pgs).

* cited by examiner

ABSORBENT ARTICLE

RELATED APPLICATION

This application is a 35 U.S.C. § 371 national phase filing of International Patent Application No. PCT/JP2013/061662, filed Apr. 19, 2013, through which and to which priority is claimed under 35 U.S.C. § 119 to Japanese Patent Application No. 2012-098253, filed Apr. 23, 2012.

TECHNICAL FIELD

The present invention relates to an absorbent article such as a disposable diaper.

BACKGROUND ART

In order to improve a wearing comfort of a wearer various methods have been devised in absorbent articles. For example, in Patent Literature 1, there is disclosure of a disposable pants as an absorbent article having a waistline gather to be fitted to a waistline of the wearer, in which an end in a longitudinal direction of an absorption member is disposed at a crotch side (inside in the longitudinal direction) than the waistline gather.

For example, if a part of a waistline gather overlaps with an absorption member, an expanding and contracting force of the waistline gather is partially different, and there is an apprehension that a disposable pant is not uniformly shrunk by the waistline gather. However, since the disposable pants described in Patent Literature 1 is disposed so that the absorption member and the waistline gather do not overlap with each other, the disposable pants is uniformly shrunk by the waistline gather, and the fitting property around the waistline of a wearer can be improved (Patent Literature 1, Paragraph 0009, FIG. 1, and FIG. 2 or the like).

CITATION LIST

Patent Literature

[PTL 1]
the publication of Japanese Patent No. 2690870

SUMMARY OF INVENTION

However, the disposables pant described above has entailed the following problems.

Bodily liquid discharged from the wearer is absorbed by an absorption member having been disposed so as to come into contact with a crotch of the wearer. However, if the absorption member does not come into intimate contact with the wearer, there may be a case in which the bodily liquid dispersed along a surface of the absorption member, and the bodily liquid leaks.

In particular, since the disposable pants of Patent Literature 1 is not disposed so that the waistline gather and the absorption member overlap with each other, the absorption member is not pulled up to the wearer's side by the waistline gather. Therefore, there may be a case in which a gap is produced between the wearer and the absorption member, the bodily liquid disperses along the surface of the absorption member, and the leakage of the bodily liquid arises.

In addition, since the absorption member of Patent Literature 1 is small in length in a longitudinal direction in comparison with the absorption member that is disposed extending outside in the longitudinal direction more significantly than the crotch region, the absorbent performance is comparatively low. Therefore, even in the case where the absorption member comes into intimate contact with the wearer, there is an apprehension that the leakage of bodily liquid arises if a large amount of bodily liquid is discharged.

Accordingly, it is an object of the prevent invention to provide an absorbent article which improves an absorption performance and a fitting property in a crotch region while enhancing the fitting property of the waistline of a wearer, and which is capable of preventing a leakage of bodily liquid.

An absorbent article having: a longitudinal direction (longitudinal direction L) extending to a body front side and a body rear side of a wearer; a widthwise direction (widthwise direction W) perpendicular to the longitudinal direction; an inner direction (inner direction IN) for facing a wearer; an outer direction (outer direction OUT) which is opposite to the inner direction, a crotch region (crotch region R3) which is adapted to be in contact with a crotch of the wearer; a front waistline region (front waistline region F1) which is disposed forward of the crotch region, and is adapted to be in contact with a waistline of the wearer; a rear waistline region (rear waistline region R2) which is disposed rearward of the crotch region, and is adapted to be in contact with the waistline of the wearer, an absorber (absorber 40) which is disposed at least at a center in a widthwise direction of the crotch region; an exterior body (exterior body 1B) which is positioned at the outer direction side of the absorber, and is disposed on a surface at a non-skin contact side of the absorbent article; and leg opening units (leg opening units 9) disposed along a leg-line of the wearer and formed in the crotch region, wherein the exterior body has an edge part (edge part 7) which is forming a part of the leg opening unit and is positioned outboard of the absorber in a widthwise direction, a rear end of the absorber is positioned in the crotch region, a waistline elastic member (waistline elastic member 3A) to expand and contract in the widthwise direction in the waistline region and a leg-holes elastic member (Front leg-holes elastic member 5F, Rear leg-holes elastic member 5R) to expand and contract along the leg opening unit are disposed at the exterior body, the leg-holes elastic member has: one pair of first expanding and contracting units (first expanding and contracting units 51) which is positioned inside in the longitudinal direction as the first extending and contracting units go to a center in a widthwise direction and which is positioned outboard of the absorber in the widthwise direction; and a second expanding and contracting unit (second expanding and contracting unit 52) which is positioned in an absorber disposition region in which the absorber is disposed between the first expanding and contracting units, and an edge part of the exterior body extends across the end of the absorber in the widthwise direction from the outside in the widthwise direction to an inside in a widthwise direction as the edge part goes to the inside in the inside in the longitudinal direction.

DESCRIPTION OF EMBODIMENTS

Figure 1:
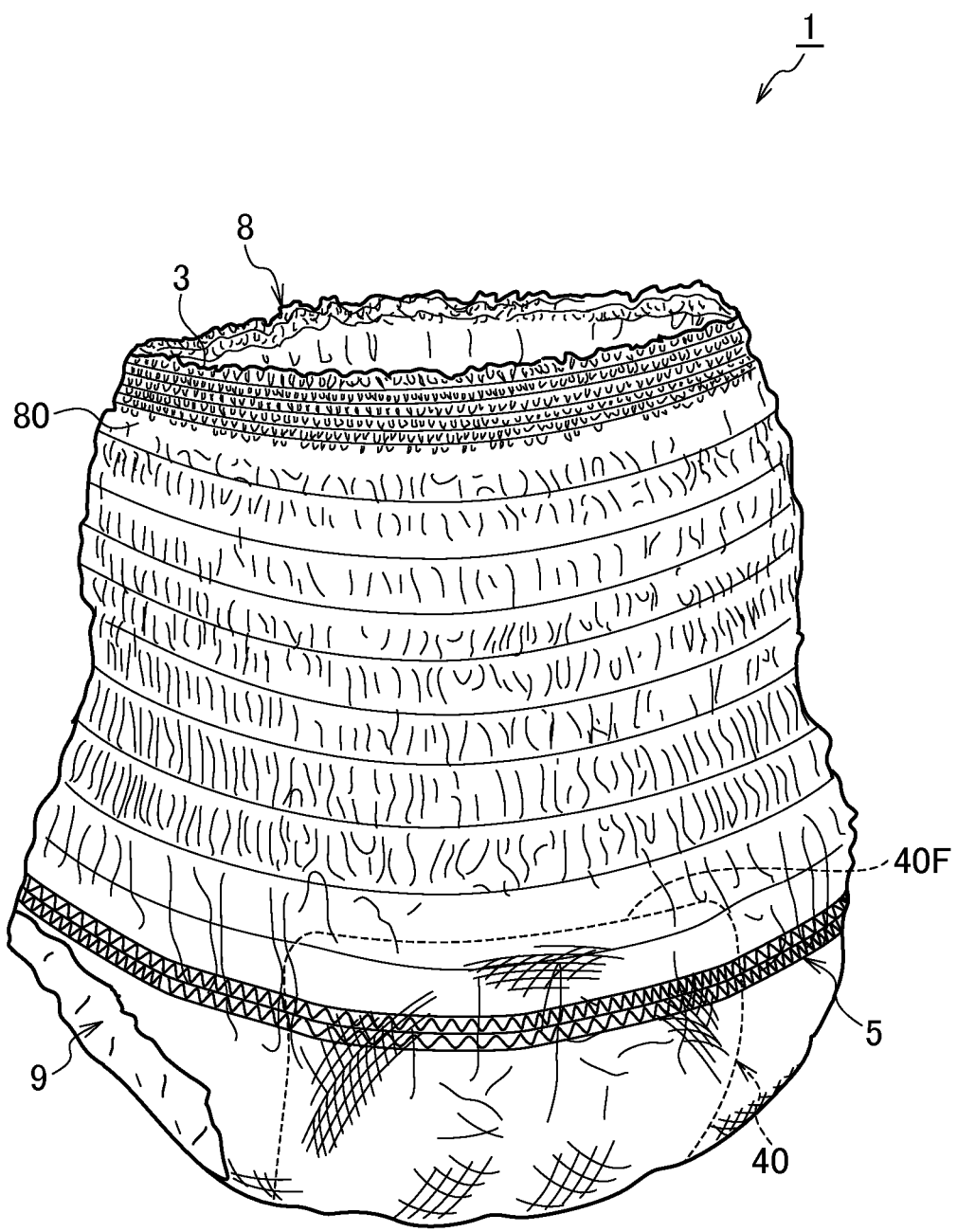
FIG. 1 is a schematic perspective view of a disposable diaper according to at least one embodiment.

Next, embodiments of a disposable diaper 1 according to the present disclosure will be described with reference to the drawings. It is to be noted that in the following description of the drawings, same or similar constituent elements are designated by same or similar reference numerals. However, it should be kept in mind that the drawings are schematic representations and are not drawn to scale unless otherwise specified. Moreover, the drawings do not necessarily reflect the actual dimensional relationships and ratios of component. Therefore, specific dimensions or the like should be determined in consideration of the following description. In addition, relations or ratios among such dimensions may be different from one drawing to another.

The disposable diaper according to the embodiment is characterized in that: in a crotch region, an end of an exterior body extending to the outside in a widthwise direction more significantly than an absorber forms a part of a leg opening unit; a rear end of the absorber is positioned in the crotch region so as not to overlap with a waistline elastic member; and in an absorber disposition region in which the absorber is disposed, an end in a widthwise direction of the exterior body is positioned inside in the widthwise direction more significantly than an end in the widthwise direction of the absorber, and a part of a leg-holes elastic member is disposed.

(1) Overall Schematic Configuration of the Disposable Diaper

Figure 2:
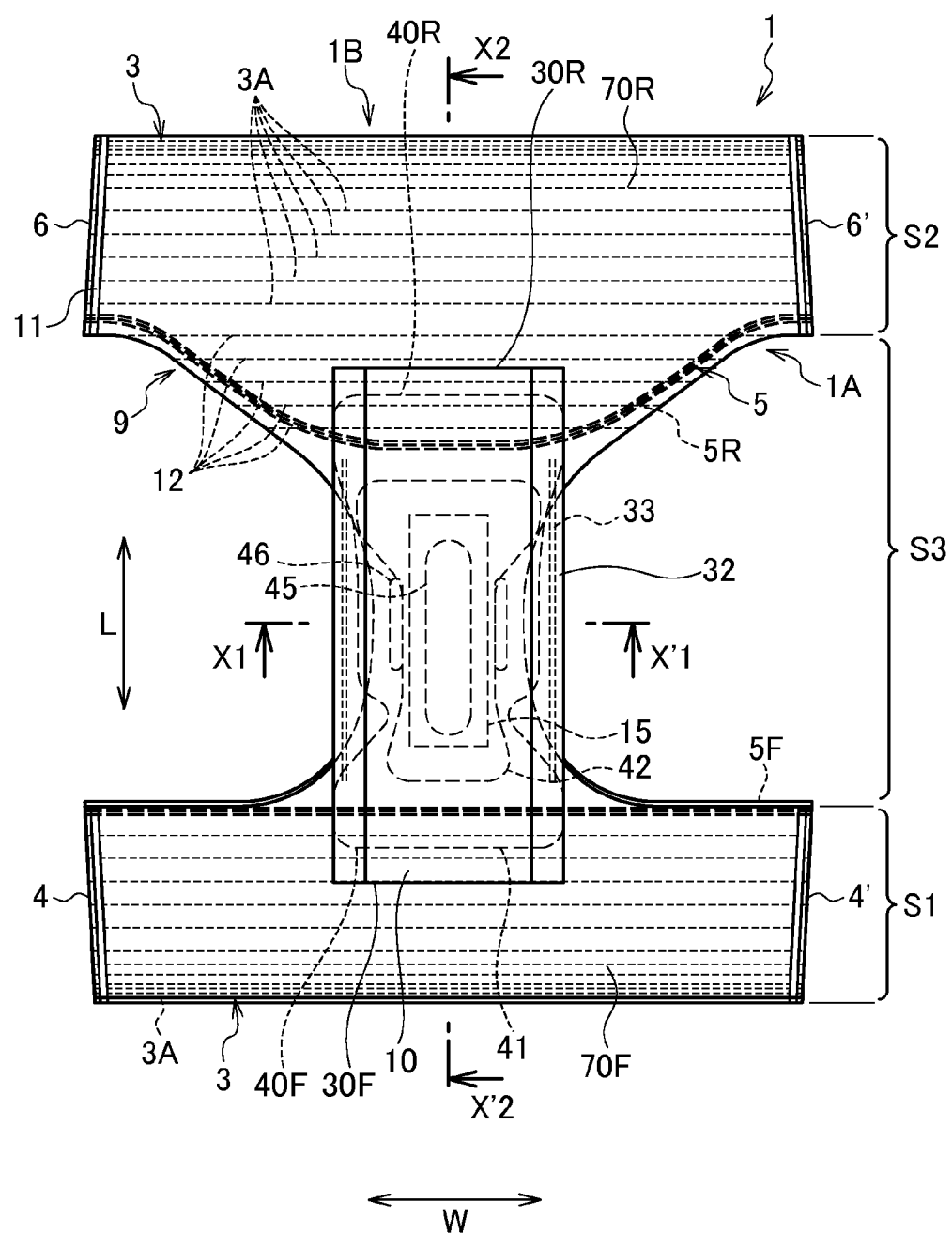
FIG. 2 is an exploded plan view of the disposable diaper according to at least one embodiment.
Figure 3:
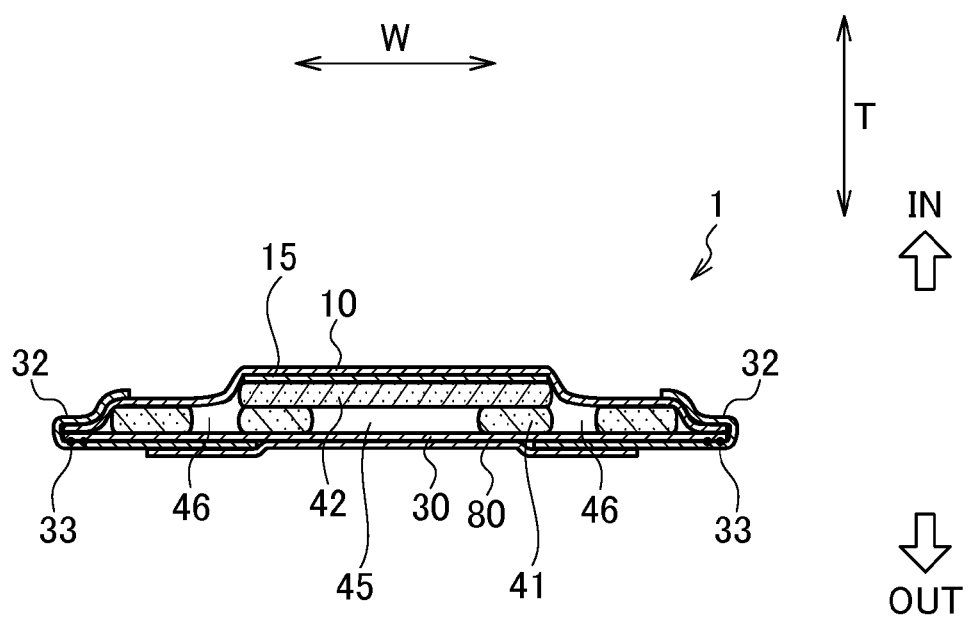
FIG. 3 is a cross-sectional view in the widthwise direction of the disposable diaper along the X1-X'1 line shown in FIG. 2.
Figure 4:
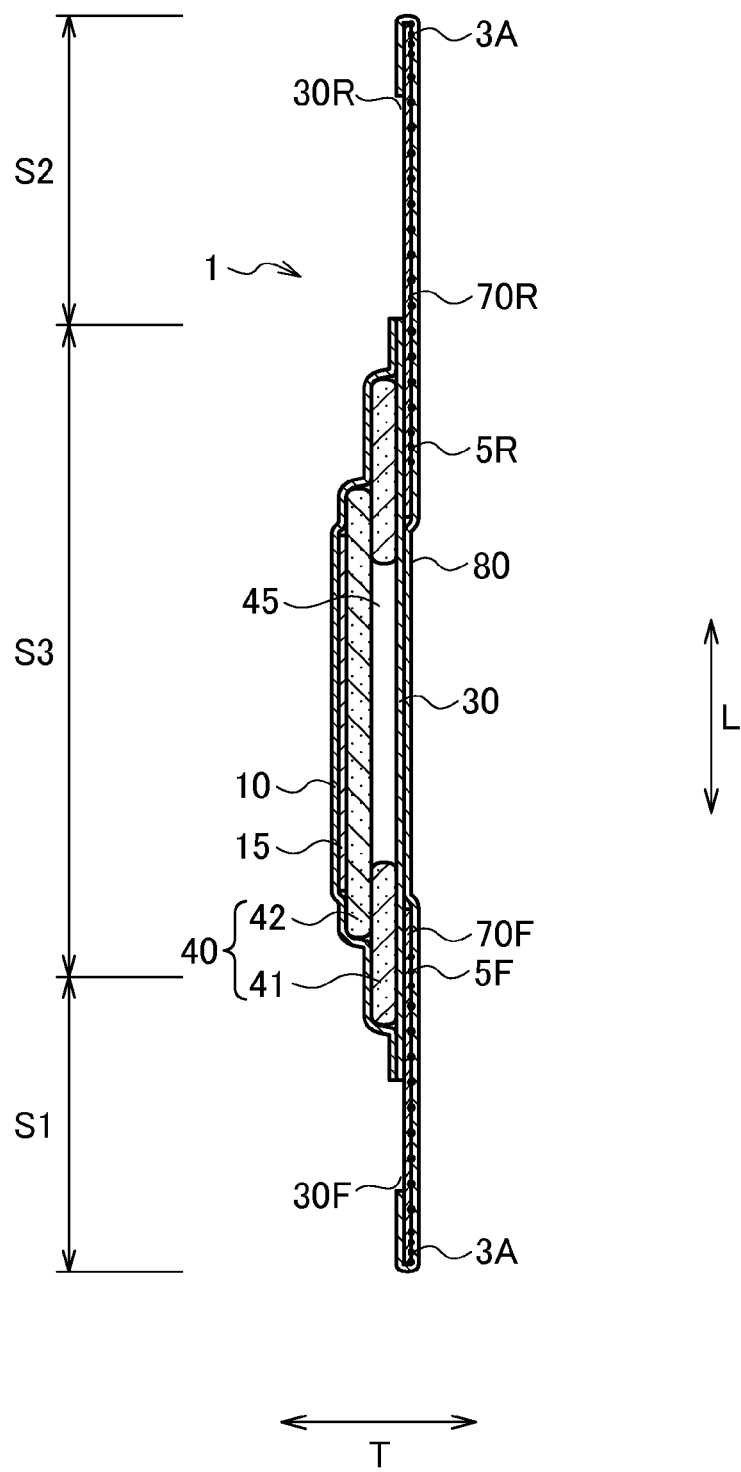
FIG. 4 is a cross-sectional view in the longitudinal direction of the disposable diaper along the X2-X'2 line shown in FIG. 2.

FIG. 1 is a perspective schematic view of a disposable diaper 1 that configures the disposable diaper in present embodiment. FIG. 2 is an exploded plan view of the disposable diaper 1 according to at least one embodiment. FIG. 3 is a cross-sectional view in the widthwise direction of the disposable diaper along the X1-X'1 line shown in FIG. 2. FIG. 4 is a cross-sectional view in the longitudinal direction of the disposable diaper along the X2-X'2 line shown in FIG. 2. The disposable diaper 1 is a pants-type disposable diaper.

A disposable diaper 1 has: a longitudinal direction L extending to a body front side and a body rear side of a wearer; a widthwise direction W perpendicular to the longitudinal direction; and a thickness direction T having an inner direction IN for facing a wearer and an outer direction OUT which is opposite to the inner direction.

The disposable diaper 1, as shown in FIG. 2, has, in a longitudinal direction L of the disposable diaper 1, a front waistline region S1 which is adapted to be in contact with a waistline of the wearer, a rear waistline region S2 is adapted to be in contact with a waistline of the wearer, and a crotch region S3 which is adapted to be in contact with a crotch of the wearer, and is positioned between the front waistline region S1 and the rear waistline region S2.

The crotch region S3 has: a central crotch region S32 which is the smallest in width when the legs are closed at the crotch of the wearer; a front crotch region S31 which is disposed between the central crotch region S32 and the front waistline region S1; and a rear crotch region S33 which is disposed between the central crotch region S32 and the rear waistline region S2.

A front waistline side edge 4 which is disposed outside in one widthwise direction of the disposable diaper 1 in the front waistline region S1 is joined with a rear waistline side edge 6 which is disposed outside in one widthwise direction of the rear waistline region S2, and a front waistline side edge 4' which is disposed outside in the other widthwise direction is joined with a rear waistline side edge 6' which is positioned outside in the other widthwise direction, whereby the disposable diaper 1 is formed to be of pants type. In the front waistline region and the rear waistline region of the disposable diaper of the pants type, a joint unit 11 of which the respective edge parts are joined with each other is formed, and the crotch region S3 is a region inner side of the joint unit 11 in the longitudinal direction.

In the disposable diaper 1, as shown in FIG. 1, there are formed: a waistline opening unit 8 disposed so as to surround the wearer's waistline and a pair of leg hole opening unit 9 disposed so as to surround the wearer's leg in a state in which it is formed in the shape of a pant. It is to be noted that a structure of the leg hole opening unit will be described later in detail.

The disposable diaper 1 includes: an absorbent main body 1A including a topsheet 10, an absorber 40, and an absorber backsheet 30 or the like; and an exterior body 1B including a foreside exterior topsheet 70F, a rear-side exterior topsheet 70R, and an exterior backsheet 80 or the like, and these constituent elements are joined to each other by an adhesive or thermal fusion bonding or the like.

The exterior body 1B includes: a foreside exterior topsheet 70F, a rear-side exterior topsheet 70R, an exterior backsheet 80, and constitutes an exterior portion of the disposable diaper 1. The exterior body 1B is arranged at outer direction side of the absorbent main body 1A, and positioned the skin non-contact surface side of the disposal diaper. The foreside exterior topsheet 70F is disposed across the front waistline region S1 and the front crotch region S31. The rear-side exterior topsheet 70R is disposed across the rear waistline region S2 and the rear crotch region S33. The foreside exterior topsheet 70F and the rearside exterior topsheet 70R are spaced from each other in the longitudinal direction, and are disposed in the thickness direction between the exterior backsheet 80 and the absorbent main body 1A.

The foreside exterior topsheet 70F and the rear-side exterior topsheet 70R can be formed by an air-through nonwoven cloth, a spunbond nonwoven cloth, a SMS nonwoven cloth, or a water-resistive film. The foreside exterior topsheet 70F and the rear-side exterior topsheet 70R according to at least one embodiment are constituted of an SMS nonwoven cloth having a basis weight of 15 g/m2 of polypropylene.

The exterior backsheet 80 lies outside when the disposable diaper is worn. Namely, the exterior backsheet is disposed on a side on which they are spaced from the wearer's skin. The exterior backsheet 80 is disposed across the front waistline region 51 and the rear waistline region S2. Ends of the exterior backsheet 80 in longitudinal direction are folded back to the skin-contact face side, and are disposed so as to envelope an end in longitudinal direction of the foreside exterior topsheet 70F (or the rear-side exterior topsheet 70R).

The exterior backsheet 80 can be formed by an air-through nonwoven cloth, a spunbond nonwoven cloth, a SMS nonwoven cloth, or a water-resistive film. The exterior backsheet 80 according to at least one embodiment is constituted of a spunbond nonwoven having a basis weight of 17 g/m2 of polypropylene.

The absorbent main body 1A includes a topsheet 10, an auxiliary sheet 15, an absorber backsheet, and a leakage preventing unit, and is disposed is provided closer to the skin contact surface than the exterior body 1B.

The topsheet 10 is a sheet that forms the skin contact surface that can be in direct contact with the skin of the wearer. The topsheet 10 is provided closer to the skin contact surface than the absorber 40. The topsheet 10 is formed by a liquid-permeable sheet, such as a hydrophilic nonwoven cloth and a hydrophilic woven cloth, an aperture plastic film, or an aperture hydrophobic nonwoven cloth. The topsheet 10 according to at least one embodiment is formed of a hydrophilic point bond nonwoven cloth having a basis weight of 23 g/m2 of polypropylene.

An auxiliary sheet 15 is joined with the non-skin contact surface side of the topsheet 10. The auxiliary sheet 15 is disposed between the topsheet 10 and the absorber 40. Providing the auxiliary sheet 15 makes it possible to increase the speed at which the bodily fluid is absorbed, and makes it possible to prevent reversal of the bodily fluid after absorption.

The topsheet 10 and the auxiliary sheet 15 according to at least one embodiment are joined by adhesive. The auxiliary sheet 15 is made of, for example, an air-through nonwoven cloth, an aperture film, or the like. The auxiliary sheet 15 according to at least one embodiment is formed of air-through nonwoven cloth (hydrophilic) having a basis weight of 30 g/m2.

The absorber 40 is joined between a composite sheet on which the topsheet 10 and the auxiliary sheet 15 are joined with each other and the absorber backsheet 30 by a hot melt adhesive. The hot melt adhesive is respectively applied to the composite sheet and the backsheet, and is applied at a respective one of the basis weights of 5 g/m2 and 8 g/m2 by a spiral coating method, for example.

The absorber 40 is disposed the center of the crotch region S3 in the widthwise direction.

The rear end 40R of the absorber 40 is disposed in the crotch region S3, and the front end 40F of the absorber 40 is disposed in the front waistline region S1. Since the length in the longitudinal direction of the absorber is small in comparison with a mode in which both of the front end and the rear end of the absorber are disposed in the front waistline region and the rear waistline region, the weight of pulp can be reduced while the base weight of the pulp of the absorber is maintained. The weight of the pulp is reduced while the base weight of the pulp is maintained, whereby material costs can be reduced without losing an absorption speed of bodily liquid.

Incidentally, in so far as the absorber 40 is concerned, it is sufficient if at least the rear end 40R be disposed in the crotch region, and the front end 40F of the absorber 40 may be disposed in the front waistline region, or alternatively, may be disposed in the crotch region.

The absorber 40 is formed of a mixed powder of ground pulp, highly absorbent polymer, and the like. The absorber 40 is configured using a first absorbent layer 41 disposed at the non-skin contact surface side of the wearer and a second absorbent layer 42 overlapping with the first absorbent layer 41 and disposed at the skin contact surface side of the wearer (see FIG. 6).

The first absorbent layer 41 has a central slit 45 constituting a central curving unit and side slit 46 constituting side curving units. The central slit 45 formed in the center of the first absorbent layer in the widthwise direction. A pair of side slits 46 is formed outboard of the central slit 45 in the widthwise direction. This diaper is constituted with central slit and side slits or the like formed on the absorber 40 so that the absorber 40 is curved when the disposable diaper 1 is worn. It is to be noted that a structure of the absorber will be described later in detail.

The absorber backsheet 30 is provided at a non-skin contact surface side of the absorber 40. The absorber backsheet 30 is formed of a sheet such as a liquid-impermeable film (for example, polyethylene).

The absorber backsheet 30 is disposed in an outer direction OUT more significantly than the absorber, and is formed of a liquid non-permeable. The absorber backsheet 30 is disposed so as to be extensive to the outside in the longitudinal direction more significantly than the absorber 40.

The rear end 30R of the absorber backsheet 30 is disposed more rearward than the rear end 40R of the absorber 40 and is disposed in the rear waistline region S2. Also, the front end 30F of the absorber backsheet 30 is disposed more forward of the front end 40F of the absorber 40 and is disposed in the front waistline region S1.

It is sufficient if the absorber backsheet 30 be disposed at least at the non-skin contact surface side of the absorber 40, and the position in the longitudinal direction is not limitative to the structure of the embodiment. For example, it may be that: the front end 30F of the absorber backsheet 30 is disposed in the front waistline region and the rear end 30R of the absorber backsheet 30 is disposed in the rear waistline region; the front end 30F of the absorber backsheet 30 is disposed in the crotch region and the rear end 30R of the absorber backsheet 30 is disposed in the rear waistline region; the front end 30F of the absorber backsheet 30 is disposed in the crotch region and the rear end 30R of the absorber backsheet 30 is disposed in the crotch region; or alternatively, the front end 30F of the absorber backsheet 30 is disposed in the front waistline region and the rear end 30R of the absorber backsheet 30 is disposed in the crotch region.

The leakage preventing unit has a leakage preventing side sheet 32 and a leakage preventing elastic member 33, and is disposed along the longitudinal direction at a widthwise end of the absorber 40. The leakage preventing side sheet 32 is provided so as to integrally envelope the topsheet 10 and the absorber backsheet 30 at both side ends in the widthwise direction W of the absorber 40.

The leakage preventing side sheet 32 is formed of a sheet such as a liquid impermeable nonwoven cloth. One end of the leakage preventing side sheet 32 in the widthwise direction is joined with a non-skin surface of the absorber backsheet 30, and the other end in the widthwise direction of the leakage preventing side sheet 32 is folded back from a lateral of absorber in widthwise direction to the top sheet side, and is joined with a face of the skin contact face side of the topsheet 10.

The leakage preventing side sheet 32 is joined with the topsheet or the like by a hot melt adhesive. In the embodiment, a plurality of hot melt adhesives was applied in basis weight of 0.1 g/m2 by bead coating method. In addition, the leakage preventing side sheet 32 is constituted with a sheet of a hydrophobic nonwoven cloth, and in the embodiment, the leakage preventing side sheet 32 is constituted with an SMS nonwoven cloth having a basis weight of 15 g/m2 of polypropylene.

The leakage preventing elastic member 33 is adhered between the absorber backsheet 30 and the leakage preventing side sheet 32 in an expanded state. The leakage preventing elastic member 33 contracts both ends in the widthwise direction of the absorber respectively in the longitudinal direction, and functions as a side elastic member.

A hot melt adhesive can be exemplified as a means for bonding the leakage preventing elastic member. In the embodiment, Spandex is employed as the leakage preventing elastic member 33, and is directly applied by V slot method. More specifically, three leakage preventing elastic members 33 are each expanded and fixed with a thickness of 780 dtex and an expansion magnification of 2.3 times.

The leakage preventing elastic members 33 are disposed so as to substantially communicate with a leg gather to be described later in a planar view. Thus, the leakage preventing elastic members and the leg gather are disposed, whereby there can be attained advantageous effects that the wearer's leg feed can be tightened so as to be surrounded, a fitting feeling of leg feed is improved, and displacement or leakage of the disposable diaper is prevented.

A waist gather 3 is provided in the front waistline region S1 and the rear waistline region S2. The waist gather 3 has an elongated waist elastic member 3A, such as a synthetic rubber, which is arranged so as to expand and contract along the widthwise direction W of the absorber 40. The waist gather 3 is continuous from one front waistline side edge 4 lying outside in the widthwise direction W of the disposable diaper 1 in the front waistline region S1 up to the other front waistline side edge 4' and is continuous from one rear waistline side edge 6 lying outside in the widthwise direction W of the disposable diaper 1 in the rear waistline region S2 up to the rear waistline side edge 6'.

The waist gather 3 is disposed in a respective one of the front waistline region S1 and the rear waistline region S2, the rear end 40R of the absorber 40 is disposed in the crotch region S3, and thus, in the longitudinal direction, the waist gather 3 and the absorber 40 are spaced from each other. For example, if the waist gather 3 and the absorber 40 overlap with each other, the expanding and contracting force of the waist gather 3 is non-uniform, and there may be a case in which a partial excessive expansion and contracting arises or a sufficient expanding and shrinking force cannot be partially obtained. However, since the waist gather 3 and the absorber 40 are spaced from each other, a distortion in expanding and shrinking force of the waist gather 3 can be restrained.

A leg gather 5 is provided around leg opening unit 9. At least a part of the leg gather 5 is disposed along the leg opening unit 9. The leg gather 5 is formed of: a front leg-holes elastic member 5F which is disposed in the front waistline region S1; and a rear leg-holes elastic member 5R which is disposed across the rear waistline region S2 and the crotch region S3.

The leg-holes elastic member 5R is disposed from the rear waistline region S2 to the crotch region S3, and is disposed toward the inside in the widthwise direction as it goes from the rear waistline region S2 to the crotch region S3. The front leg-holes elastic member 5F is disposed along the widthwise direction in the front leg-line region S1.

Figure 5:
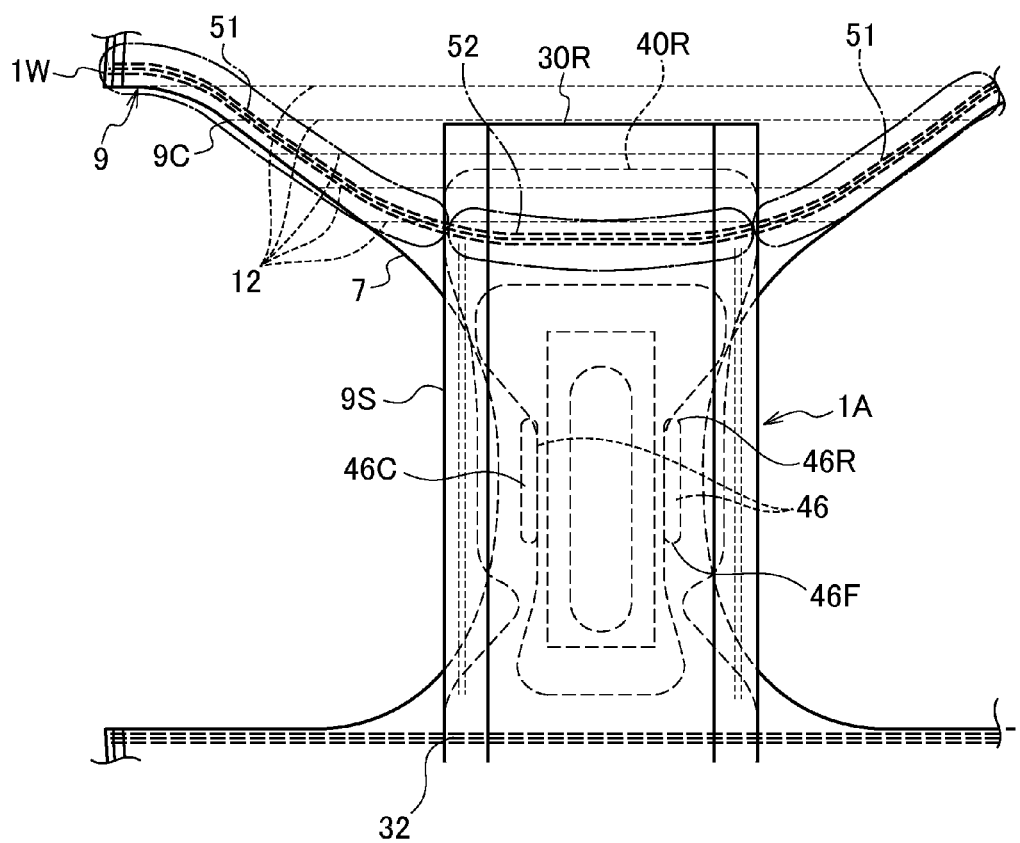
FIG. 5 is a partially enlarged view of a leg opening unit in the exploded plan view shown in FIG. 2.

The front leg-holes elastic member 5F and the rear leg-holes elastic member 5R each, as shown in FIG. 5, have: one pair of first expanding and contracting units 51 which extend to the inside in the longitudinal direction as they go to the center in the widthwise direction at the outside in the widthwise direction more significantly than the absorber; and a second expanding and contracting unit which is positioned in the absorber disposition region in which the absorber is disposed, between such one pair of the first expanding and contracting units. The first expanding and contracting units 51 and the second expanding and contracting unit 52 work together, and function to pull up the absorber to the wearer's side. In FIG. 5, a region in which the first expanding and contracting units 51 are disposed and a region in which the second expanding and contracting unit 52 is disposed are indicated by surrounding these regions by the single-dotted chain line.

Incidentally, in so far as the front leg-holes elastic member 5F and the rear leg-holes elastic member 5R are concerned, it is sufficient if the first expanding and contracting units 51 and the second expanding and contracting unit 52 be respectively disposed outside in the widthwise direction more significantly than the absorber 40 and at least a part in the absorber disposition region, and do not always need to be disposed all over the region in the widthwise direction. For example, the second expanding and contracting unit 52 may be divided into a plurality of sections at the center in the widthwise direction of the absorber disposition region, or alternatively, the first expanding and contracting units 51 may be respectively divided into a plurality of sections at one or more sites.

However, it is desirable that at least either one of the front leg-holes elastic member 5F and the rear leg-holes elastic member 5R be disposed across an end in the widthwise direction of the absorber. According to such a structure, the absorber can be pulled up to the wearer's side by the front leg-holes elastic member 5F and/or the rear leg-holes elastic member 5R.

In the rear crotch region S33, a crotch elastic member 12 is disposed. The crotch elastic member 12 is arranged so as to expand and contract along a widthwise direction W between a front end of the rear leg-holes elastic member 5R and a front end of a waist elastic member. By providing the crotch elastic member 12, any slackness or wrinkle of the exterior body 1B between the waist gather 3 and the leg gather 5 is prevented, and the fitting property can be enhanced. In particular, between in the longitudinal direction between the waist gather 3 and the leg gather 5, a rear end of the absorber is disposed, the intimacy of the rear end of the absorber is enhanced by the waist gather, and a leakage of bodily liquid can be prevented.

The front leg-holes elastic member 5F is disposed between the foreside exterior topsheet 70F and the exterior backsheet 80, and the rear leg-holes elastic member 5R is disposed between the rear-side exterior topsheet 70R and the exterior backsheet 80. Also, the waist elastic member 3A is bonded between the foreside exterior topsheet 70F or the rear-side exterior topsheet 70R and the exterior backsheet 80. The crotch elastic member 12 is arranged between the foreside exterior topsheet 70F or the rear-side exterior topsheet 70R and the exterior backsheet 80.

In the embodiment, in so far as the waist elastic member 3A is concerned, a hot melt type adhesive is applied in a V-slot approach, and the elastic member is adhered and fixed between an exterior topsheet and an exterior backsheet. In so far as the front leg-holes elastic member 5F and the rear leg-holes elastic member 5R are concerned, a hot melt type adhesive is applied to the exterior topsheet side in a spiral approach, and a hot melt type adhesive is applied to the exterior backsheet side in a control seam approach, and these elastic members are adhered and fixed between the exterior topsheet and the exterior backsheet, In so far as the crotch elastic member 12 is concerned, a hot melt type adhesive is directly applied to the crotch elastic member 12 in the V-slot approach, and a hot melt type adhesive is applied to the exterior backsheet side in the control seam approach, and further, the crotch elastic member is adhered and fixed between the rear exterior topsheet and the rear exterior backsheet.

The waist elastic member 3A, the front leg-holes elastic member 5F, and the rear leg-holes elastic member 5R are composed of spandex. Six waist elastic members 3A each are fixed to be expanded in thickness of 940 dtex and at an expansion magnification of 3.5 times in the vicinity of the waistline opening unit 8, and the eight waist elastic members each are fixed to be expanded in longitudinal manner in thickness of 780 dtex and at an expansion magnification of 3.0 times inside in the longitudinal direction more significantly than the six elastic member. Three front leg-hole elastic members 5F and three rear leg-holes elastic members 5R each are fixed to be expanded in thickness of 780 dtex and at an expansion magnification of 1.5 times to 3.5 times. It is to be noted that the thicknesses, the expansion magnifications, and the numbers of waist elastic members 3A, front leg-holes elastic members 5F, and rear leg-holes elastic members 5R can be variously set without being limitative thereto. Five crotch elastic member 12 each are fixed to be expanded in thickness of 780 dtex and at an expansion magnification of 2.0 times.

Incidentally, it is desirable that an expansion stress of the crotch elastic member 12 be lower than an expansion stress of a leg-holes elastic member and be lower than an expansion stress of the waist elastic member. According to such a structure, at the time of wearing, a region in which the crotch elastic member 12 is disposed is easily made expandable along the body line, any slackness or wrinkle of the exterior body 1B between the waist gather 3 and the leg gather 5 is prevented, and the fitting property can be enhanced.

Also, in so far as the expansion stresses of the front leg-holes elastic member 5F and the rear leg-holes elastic member 5R are concerned, it is desirable that the expansion stress of the second expanding and contracting unit is lower than the expansion stress of the first expanding and contracting unit. According to such a structure, when the absorber 40 is pulled up to the wearer's side, the second expanding and contracting unit is easily expandable earlier than the first expanding and contracting unit. Therefore, a pulling force along the line of the leg opening unit easily works, the absorber is easily pulled up, and the disposable diaper fits to the wearer's body, and an advantageous effect of preventing a displacement of the disposable diaper or leakage can be attained. Further, the expansion stress of the second expanding and contracting unit is lower than the expansion stress of the first expanding and contracting unit, thereby restraining excessive pulling inside in the widthwise direction by the second expanding and contracting unit, and the first expanding and contracting unit appropriately easily fits along the leg opening unit.

It is to be noted that the expansion stress of the elastic member can be measured as follows, for example.
(1) An elastic member forming a convex portion is cut out together with a material pinching the elastic member so as to entirely include the elastic member in a widthwise direction. Specifically, in a wearing article according to the embodiment, a material pinching a crotch elastic member, a leg-holes elastic member, and a waist elastic member which are disposed on a three by three pieces basis at intervals of 5 mm is cut out by 13 mm in width×100 mm in length in a state in which the material is expanded so as not to produce slackness. In a similarly expanded state, marking is carried out 10 mm inside from a respective one of both ends in the longitudinal direction. For measurement of the expansion stress, there was used a tension testing instrument (for example, model: 5564) available from Insuron Japan Company Limited, or alternatively, an auto graph (for example, model: AGS-1kNG) available from Shimadzu Corporation.
(2) The sample of item (1) above is pinched by an upper chuck so that one marking portion is set at a chuck inside end, and is punched by a lower chuck so that the other marking portion is set at a chuck inside end. A length dimension of the sample between the chucks is 80 mm. It is to be noted that in the case where a length which is effective as a gather of an elastic member is shorter than 100 mm, a length which is 20 mm shorter than the shortest length of the length of the elastic member which is effective as the gather is set at a length of the sample between the chucks. An initial distance between the chucks is set to be shorter than a length at the time when the sample contracts (a natural length) so that a tension of the sample is not initially applied. These chucks are pulled in a vertical direction under the condition of 100 mm/min so as to be spaced from each other, and the sample is expanded.
(3) A length dimension between the chucks of the sample when the material pinching the elastic member expands without slackness is set to 100%, the sample is expanded until the length dimension between the chucks of the sample has been 90%, the stress at the time of expansion of the sample at that time is measured, and the measured stress is set as an expansion stress of the elastic member. That is, in the embodiment mentioned above, the stress is measured at the time of expansion when the sample is expanded up to 72 mm which is 90% with respect to the length dimension of 80 mm which is 100% of the sample.

As a manufacturing method of the absorbent article thus structured, for example, the absorbent article can be manufactured by a method including the steps of: molding a first absorbent layer of an absorber; molding a second absorbent layer of the absorber; jointing the first absorbent layer and the second absorbent layer with each other; conveying the absorber or the like by a belt conveyor or the like and then bonding the conveyed absorber with a sheet material such as a topsheet in the course of conveyance. It is to be noted that other steps may be those in which manufacturing can be carried out in accordance with a publicly known manufacturing method.

Also, in the case where central slits or side slits are provided in both of the first absorbent layer and the second absorbent layer, there may arise a displacement at the time when the first absorbent layer and the second absorbent later are overlapped with each other. For example, if a displacement arises in a widthwise direction, the width of one pair of side slits disposed at the left and right is reduced, a regular deformation cannot be made, an unbalanced absorber at the left and right is produced, and there is an apprehension that the absorptivity or the wearing comfort is adversely affected. However, a central slit or a side slit is provided in either one of the first absorbent layer and the second absorbent layer, whereby a displacement of the side slit or the like can be prevented.

For each of the members that configure the disposable diaper 1 mentioned above, for example, the materials described in Japanese Unexamined Patent Application Publication No. 2006-346439 may be employed.

(2) Shape of Leg Opening Unit

FIG. 5 is a partially enlarged view of a leg opening unit in the exploded plan view shown in FIG. 2. A leg opening unit 9 has an inclination unit 9C toward the outside in a widthwise direction as it goes to a rear side in a region outside in the widthwise direction more significantly than the absorber 40. The inclination unit 9C is formed in a curves shape in a planer view. An edge part 1W of the exterior body 1B extends to the outside in the widthwise direction more significantly than the absorber in the crotch region.

An outside end in the widthwise direction of the exterior body 1B is disposed to be concaved inside in the widthwise direction more significantly than the absorbent main body 1A in the absorber disposition region in which the absorber is disposed (the region overlapping with the absorber in the planer view). In the region, the outside end in the widthwise direction of the absorber forms a linear leg opening unit 9. That is, the leg opening unit 9 is composed of: an inclination unit 9C which is composed of an edge part from the widthwise outside end to the widthwise inside of the exterior body 1B in the crotch region; and a parallel portion 9S along the longitudinal direction, which is composed of an edge part outside in the widthwise direction of the absorbent main body 1A.

The leg opening unit 9 comes into intimate contact with a leg-line of a wearer. In the widthwise direction, between the leg opening units 9, an absorber 40 is disposed. In a state in which the wearer wears the disposable diaper 1, one pair of leg opening units 9 are respectively disposed along the leg-line of the wearer, the absorber 40 therebetween is pulled up to the outside in the widthwise direction by the leg opening units, and a state opposite to a crotch of the wearer is maintained.

The leg opening unit outside in the widthwise direction more significantly than the absorbent main body 1A is composed of an edge part of the exterior body 1B, and the absorber is pulled up along the edge part of the exterior body 1B. Since the edge part 7 of the exterior body is across a width end of the absorber, the absorber can be pulled up to the wearer's side at the edge part of the exterior body.

Further, since the absorber and the leg-holes elastic member overlap with each other, the absorber can be pulled up to the wearer's side by the leg-holes elastic member. Therefore, by the leg-holes elastic member and the edge part of the exterior body, the absorber is brought into intimate contact with the body, the fitting property is enhanced, and the leakage can be reduced.

(3) Structure of the Absorber

Figure 6:
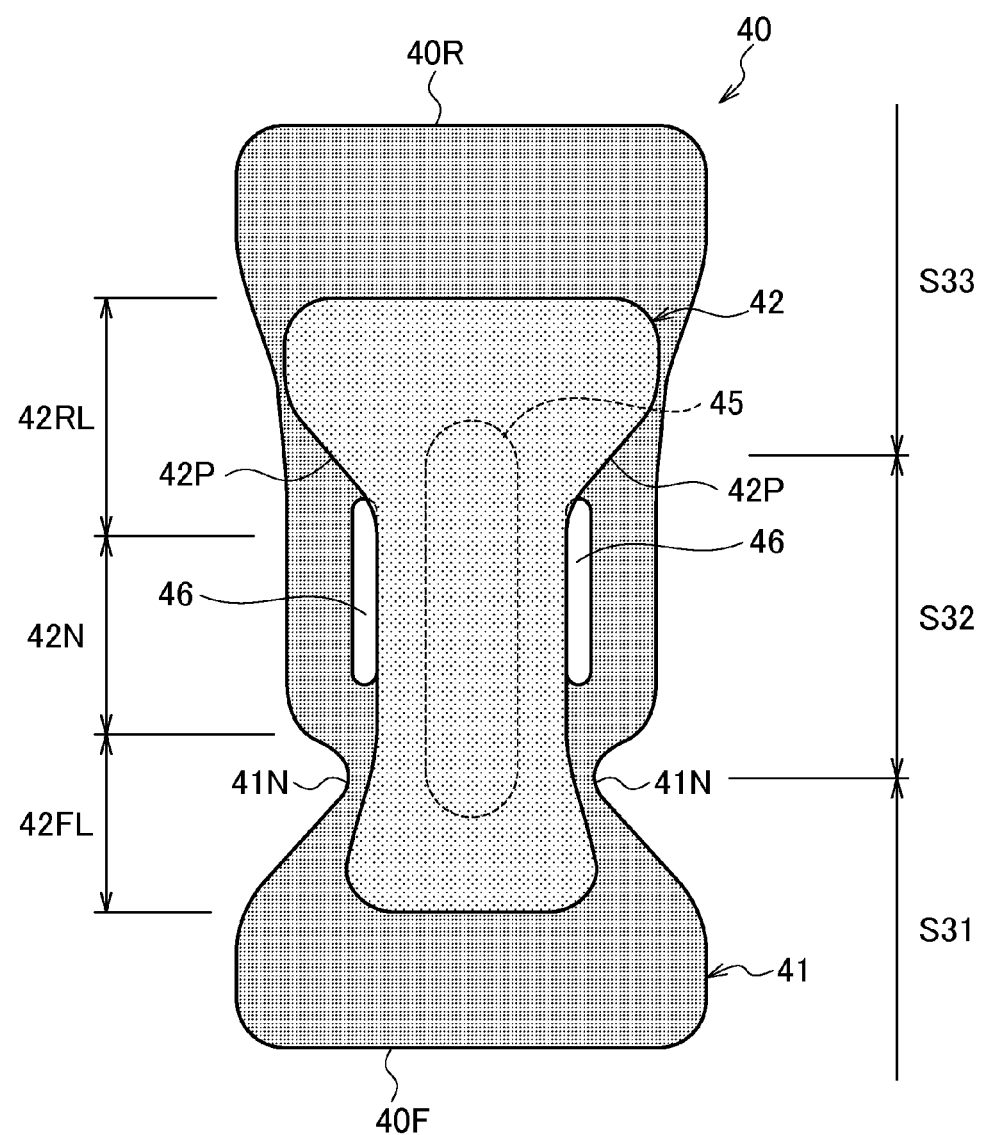
FIG. 6 is a plan view of an absorber according to at least one embodiment.
Figure 7:
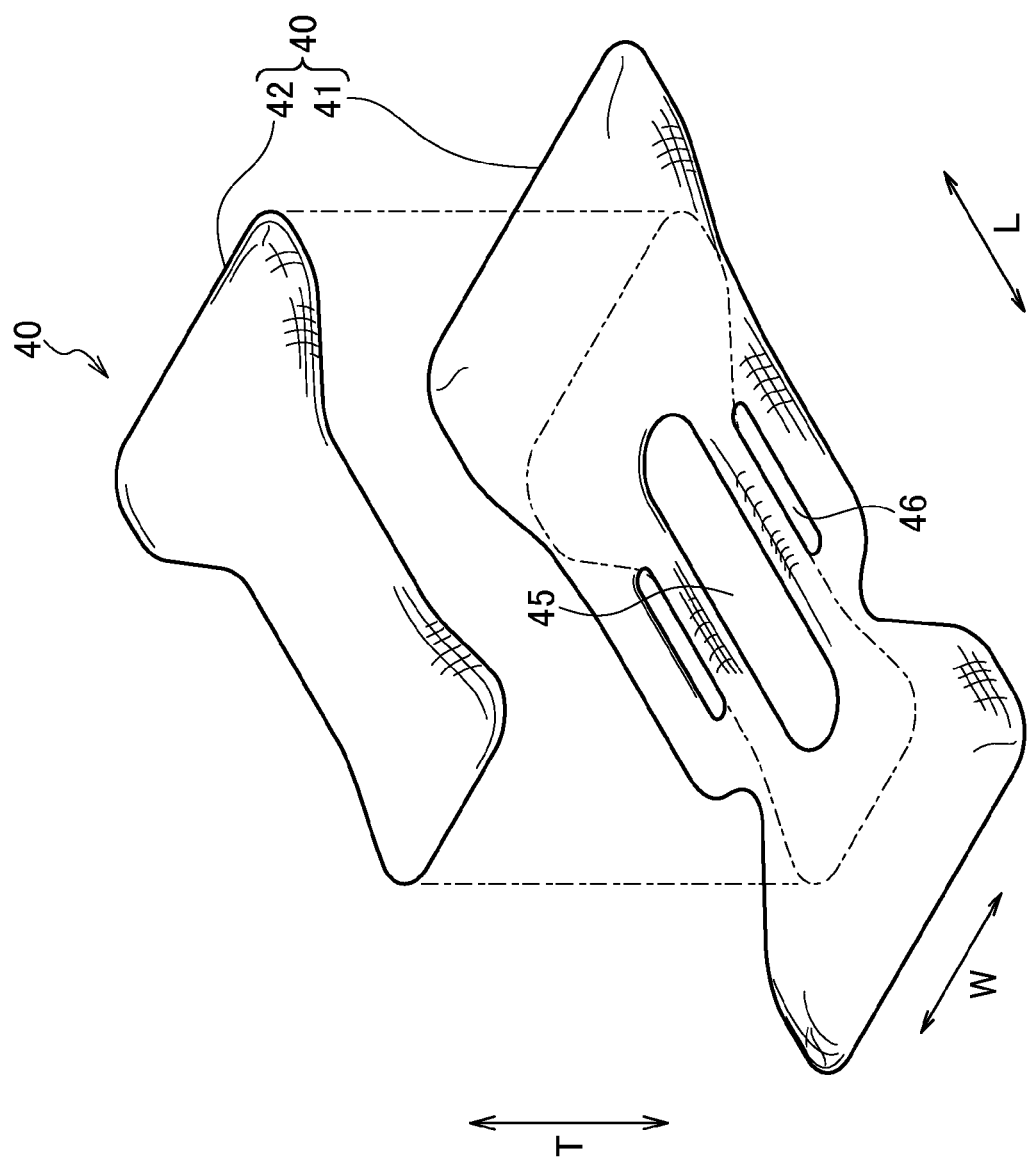
FIG. 7 is an exploded perspective view of an absorber according to at least one embodiment.

FIG. 6 is a plan view of the absorber 40. FIG. 7 is an exploded perspective view of an absorber according to at least one embodiment. As illustrated in FIG. 6 and FIG. 7, the absorber 40 has a first absorbent layer 41, and a second absorbent layer 42 positioned at the skin contact surface side than the first absorbent layer 41. The first absorbent layer 41 is positioned at the non-skin contact surface side of the wearer, and the second absorbent layer 42 is positioned at the skin contact surface side of the wearer.

The absorber 40 is disposed across the front waistline region S1 and the crotch region S3. A length in the longitudinal direction of the first absorbent layer 41 is greater than a length in the longitudinal direction of the second absorbent layer 42. The first absorbent layer 41 is disposed across the front waistline region S1 and crotch region S3, and the second absorbent layer 42 is disposed in the crotch region S3. A length in the widthwise direction of the first absorbent layer 41 is greater than a length in the widthwise direction of the second absorbent layer 42. The first absorbent layer 41 overhangs to the outer side in the widthwise direction more significantly than the second absorbent layer 42.

The first absorbent layer 41 and the second absorbent layer 42 are configured from cotton-like pulp and highly polymerized absorbent polymer (SAP). The absorber 40 can be formed by mixing, for example, 100 to 500 g/m2 pulp and 0 to 500 g/m2 SAP. The first absorbent layer 41 and the second absorbent layer 42 according to the present embodiment are formed from a mixture of 260 g/m2 pulp and 160 g/m2 SAP.

In the first absorbent layer 41, the central slit 45 and a pair of side slits 46 are formed. The central slit 45 has a longitudinally elongated shape extending along the longitudinal direction L, and is formed across the central crotch region S32, the front crotch region S31, and the rear crotch region S33. The central slit 45 is thus formed, whereby a central portion in the widthwise direction of the absorber can be easily curved in a convex manner in an inner direction IN which is the wearer's side. Also, the dispersion property of bodily liquid or the like in the longitudinal direction of the absorber is enhanced, the bodily liquid or the like is dispersed in a wide range, and the absorption performance can be improved.

One pair of side slits 46 are respectively formed outside in the widthwise direction more significantly than the central slit 45. The side slit 46 has a longitudinally elongated shape extending along the longitudinal direction L, and is formed in the central crotch region S32. The side slit 46 is formed in the absorber 40 along the longitudinal direction L so that the absorber 40 curves in a convex manner in an outer direction OUT, namely, so that the absorber 40 curves in a convex manner which is opposite to the central slit 45.

Figure 8:
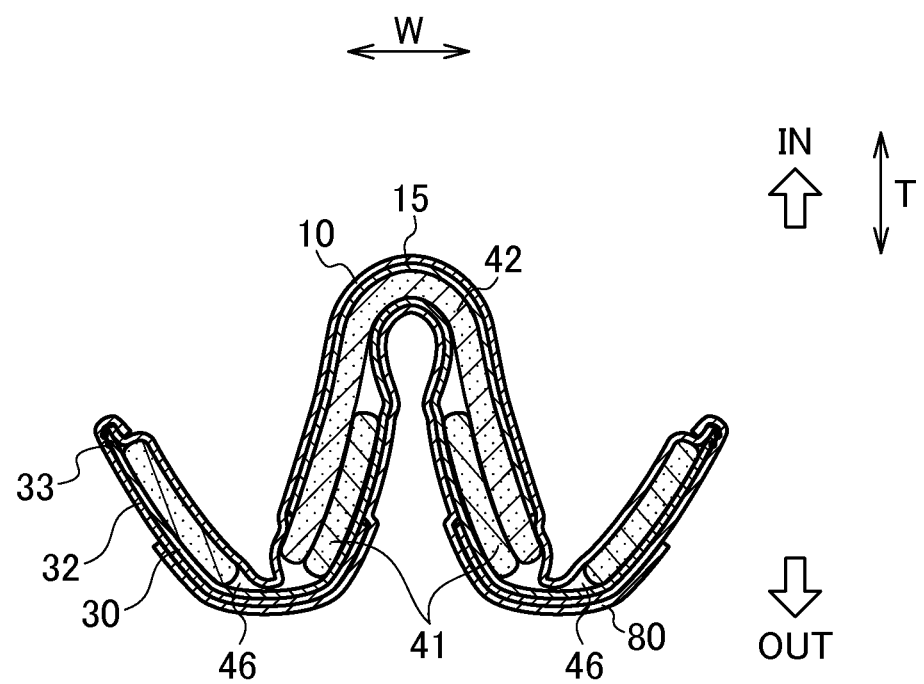
FIG. 8 is a cross-sectional view along the X1-X'1 line that schematically illustrates the wearing state of the disposable diaper according to at least one embodiment.

Next, a deformation aspect of the absorber will be described. FIG. 8 is a cross-sectional view (with reference to the X1-X'1 line of FIG. 2) that schematically illustrates the wearing state of the disposable diaper 1. As illustrated in FIG. 8, when the disposable diaper 1 is worn, the crotch region S3 of the absorber comes up against the crotch of the wearer. Due to the legs and the like of the wearer, force is applied on the absorber inwardly in the widthwise direction. The absorber 40 is curved in the inner direction IN and the outer direction OUT such that the side slits 46 and the central slit 45 are reference points. The cross-sectional shape of the disposable diaper 1 along the widthwise direction W is deformed in a wavelike manner, the central crotch region S32 of the crotch region S3 of the absorber 40 enters a regularly folded state.

The absorber is thus folded, whereby even in the case where an area of the absorber is increased so as to ensure an absorption performance, the absorber 40 in the crotch region S3 is appropriately folded to enable the absorber 40 and an excretion portion to come into intimate contact with each other. Therefore, as in the absorber according to the embodiment, in the crotch region, the absorber 40 is extended outside in the widthwise direction with respect to the outside end in the widthwise direction of the exterior body 1B, whereby an area of the absorber that is disposed in the crotch of the wearer can be increased. As a result, the absorption performance can be improved.

By increasing the area of the absorber that is disposed in the crotch region, for example, as in the embodiment, the rear end of the absorber is disposed in the crotch region, and even in a mode in which the length in the lengthwise direction of the absorber is comparatively small, the absorption performance is improved, and the leakage of bodily liquid can be restrained.

The top surface of the absorber 40, which becomes convex in the inner direction IN due to the central slit 45, comes into contact with the crotch of the wearer. The portion where the convex portion, caused by the central slit 45, is formed is configured from only the second absorbent layer 42, and is comparatively thinner. On the other hand, the first absorbent layer 41 and the second absorbent layer 42 overlap between the convex portion caused by the central slit and the convex portion caused by the side slits. This overlap portion is comparatively thicker and has high rigid. The high rigid portion between the central slit and the side slits makes it possible to support the convex portion caused by the central slit, and makes it possible to enhance the stability of the convex shape caused by the central unit.

When the wearer closes both legs, with respect to the cross-sectional shape of the disposable diaper 1, the absorber is folded over at the central slit and the side slits and is compactly disposed below the crotch of the wearer in a state of close mutual contact. Therefore, the absorption performance can be ensured while a sense of discomfort in the vicinity of the crotch portion is restrained.

At such a time, the convex portion formed by the central slit 45 is positioned so as to be in contact with the crotch of the wearer. On the other hand, the convex portion formed by the side slits 46 is convex toward the non-skin contact surface, and is positioned so as not to be in contact with the excretion opening of the wearer.

Because the absorber is in close contact at the crotch of the wearer, leakage of the bodily fluid can be prevented even in a case where urine slowly is excreted, which would run along the skin.

In the folded state, a concavity expanding in the longitudinal direction is formed at the curving unit in the portion of the absorber separated from the skin, and therefore the bodily fluid can be spread outward in the longitudinal direction and side leakage can be prevented.

Further, since a side curving unit forms a concavity portion, excretions is prone to easily get into the concavity portion, and a direct contact between the wearer's skin and the excretions can be restrained.

A convex portion formed by the central curving unit is small in thickness and high in height. Therefore, a sectional shape when the disposable diaper 1 is worn and the absorber 40 is deformed is a tapered shape narrowing from a non-skin contact surface side to a skin contact surface side. A convex portion formed by the central curving unit is prone to be easily inserted into a narrow gap of the crotch portion, and is also prone to easily come into intimate contact with the excretion opening. Since the urine opening and the absorber come into intimate contact with each other, the excreted urine can be speedily absorbed. Further, the absorber is prone to be easily included in the gap of the wearer's crotch portion, and a feeling of discomfort is hardly felt. Also, folding is carried out so that the thickness of the absorber is small at a portion which is close to the skin of the wearer's crotch portion, and the thickness is large at a portion which is distant from the skin, and therefore, fitting can be obtained without a sense of discomfort.

Next, a detailed description of a structure of the first absorbent layer 41 and the second absorbent layer 42 will be given. The first absorbent layer 41 is smaller in length in the widthwise direction from the front crotch region S31 to the central crotch region S32, and is smaller in length in the widthwise direction from the rear crotch region S33 to the central crotch region S32. In the first absorbent layer 41, a concavity portion 41N which is recessed inside in the widthwise direction from the front crotch region S31 to the central crotch region S32 is formed. The concavity portion 41N is positioned more forward than the side slit 46, and functions as a deformation restraining portion.

Since the concavity portion 41N is formed more forward than the side slit 46, a deformation exerted by the side slit 46 can be hardly transmitted to the front waistline region 51. Therefore, at the front side more significantly than the concavity portion 41N, a deformation of the absorber 40 in a convex shape is restrained, and the absorber 40 can be disposed along the wearer's skin.

The second absorbent layer 42 is formed in the shape of a substantial hourglass. The second absorbent layer has: a narrow part 42N which is positioned at a central portion in a longitudinal direction and has a predetermined width in a widthwise direction W; a front wide part 42FL which is positioned at a front side of the narrow part 42N and is large in width than the narrow part; and a rear wide part 42RL which is positioned at a rear side of the narrow part 42N and is large in width than the narrow part. A side end of the narrow part 42N, a side end of the front wide part 42FL, and a side end of the rear wide part 42RL are connected to each other by way of a curve, and the second absorbent layer 42 has an hour glass-type planar shape.

The first absorbent layer 41 and the second absorbent layer 42 are formed as one part by being pressed along the thickness direction T. Note that the first absorbent layer 41 and the second absorbent layer 42 may also be formed as one part by an adhesive and thermal fusion bonding. Furthermore, in the absorber 40, the first absorbent layer 41 is positioned at the non-skin contact surface side and the second absorbent layer 42 is positioned at the skin contact surface side, but the second absorbent layer 42 may be positioned at the non-skin contact surface side and the first absorbent layer 41 may be positioned at the skin contact surface side.

In the widthwise direction, an outside end of the narrow part 42N and an inside end of the side slit 46 are coincident with each other. According to such a structure, a difference in rigidity of the absorber 40 is formed at an end in the widthwise direction of the side slit 46, and the absorber can be stably bent while the side slit 46 is defined as a start point.

Further, as shown in FIG. 2, in the widthwise direction, an end of the auxiliary sheet 15 is positioned inside more significantly than the slide slit. Rigidity is different depending on a region in which the auxiliary sheet 15 is disposed and a region in which the auxiliary sheet 15 is not disposed (the region outside in the widthwise direction more significantly than the end in the widthwise direction of the auxiliary sheet 15). The difference in rigidity exerted by the presence or absence of the auxiliary sheet is provided, whereby curving can be easily made while a side curving unit which is composed of the side slit 46 is defined as a start point.

Also, the end in the widthwise direction of the rear wide part 42RL extends from the inside of the widthwise direction of the slide slit to the outside in the widthwise direction at the rear side more significantly than the side slit. The end in the widthwise direction of the rear wide part functions as a deformation restraining portion 42P.

The deformation restraining portion 42P is disposed more rearward than the slide slit. The deformation restraining portion 42P is disposed so as to extend from the inside of the widthwise direction to the outside in the widthwise direction as it goes from the narrow part 42N of the second absorbent layer 42 to the rear side. In a region which is more forward than the deformation restraining portion 42P, only the first absorbent layer 41 is disposed, whereas in a region more rearward than the deformation restraining portion 42P, the first absorbent layer 41 and the second absorbent layer overlaps with each other, and a difference in rigidity of the absorber arises at the deformation restraining portion. Therefore, deformation at the front side more significantly than the deformation restraining portion 42P is hardly transmitted to the rear side.

The deformation restraining portions are provided forward and rearward of the side slit 46, whereby the absorber is disposed in the crotch region while it is deformed, whereas transmission of the deformation to the rear waistline region and the front waistline region can be restrained. Further, even in the case where the front waistline region S1 and the rear waistline region S2 of the absorber are deformed, since the deformation is hardly transmitted to the crotch region, the absorber 40 can be stably folded in a convex manner in the crotch region S3.

In addition, the amount of water preservation of the absorber 40 is 300 g or more. The term "amount of water preservation" in the embodiment means the maximum amount of water that is capable of retaining the water content absorbed by the absorber, and specifically means the amount of water that can be retained even in the case where dewatering is carried out by 150G. The amount of water reservation can be specifically obtained by the measurement method described below.

First, as instruments to be used, physiological saline (0.9% NaCl solution), an acrylic plate (nominal dimension: 320 mm×545 mm, thickness: 3 mm to 5 mm, and weight: 400 g to 600 g), a dewatering machine (150G), and a wire net (standard wire net: punched hole: 5 φ and distance between holes: 5 mm) are prepared.

Next, samples targeted to be measured are taken. After the weight of one diaper has been measured, a waist gather (WG), a leg gather (LG), and a solid gather (LSG) are cut, and the diaper is fattened. At the time of cutting, extreme care must be taken so as not to cut to the absorber. In addition, the number of samples taken is n=5.

As a procedure, first, an absorber of the diaper is immersed while the absorber is pressed by hand in about 20 L of the physiological saline in a state in which the absorber is oriented downward. The physiological saline enables measurement of up to six diapers, and if measurement of more than six diapers is carried out, the density varies, and thus, replacement is needed. After the diaper has been immersed, the immersed diaper is left as it is for 30 minutes in that state. After the elapse of 30 minutes, the diaper is removed and folded so that the exterior body 1B is inside of the diaper, and the waist gather 3 is pinched with a clip and then is hanged on a beam. The gather is left as it is for 10 minutes in this state. After the elapse of 10 minutes, the weight of the diaper is measured, and the amount of water absorption is obtained from a difference from the initial weight.

Next, diapers (up to three diapers) of which the amounts of water absorption each are obtained by carrying out the procedures mentioned above are put in the dewatering machine, the diapers are arranged with the absorbers being oriented outside so that the diapers do not overlap with each other, and dewatering of 150G is carried out for 90 seconds. After the dewatering, the weight of the diaper is measured, and the amount of water preservation is obtained from a difference from the initial weight.

(4) Modification Example

Next, the disposal diapers according to modification examples are explained with reference to drawings. Note that the same symbols are used to denote portions similar to those of the first embodiment, and the differences between the embodiments are mainly explained below.

Figure 9:
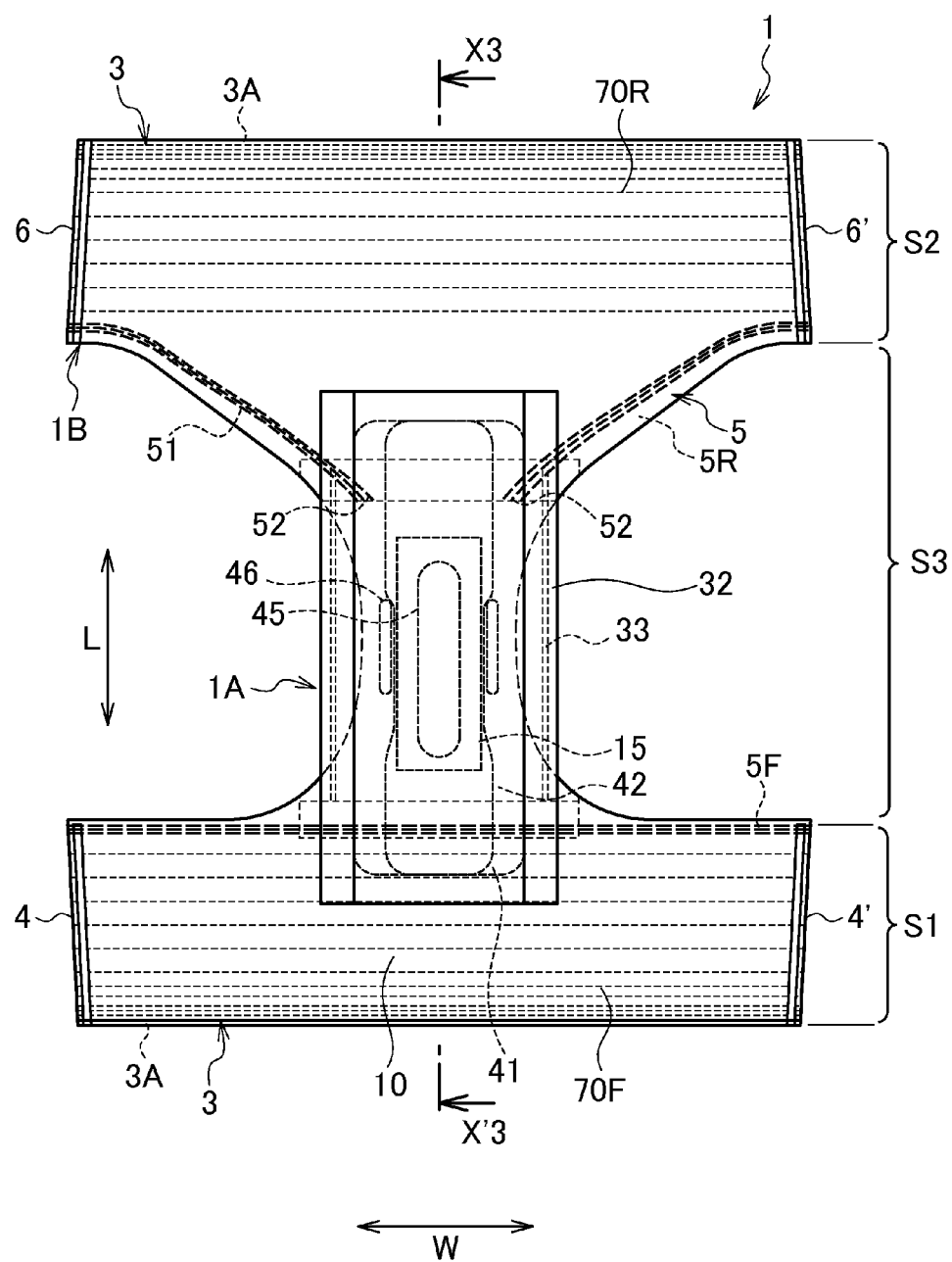
FIG. 9 is an exploded plan view of a disposable diaper according to modification example.
Figure 10:
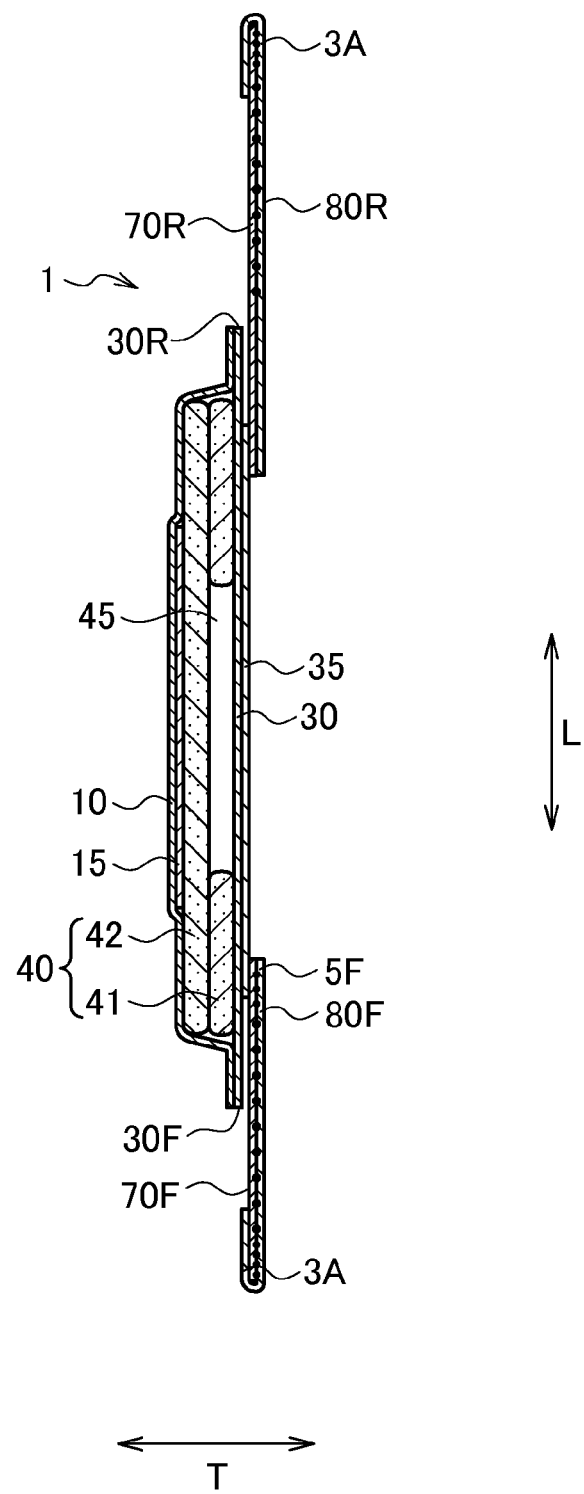
FIG. 10 is a crosswise cross-sectional view in the longitudinal direction of the disposable diaper along the X3-X'3 line shown in FIG. 9.

FIG. 9 is a plan view of a disposable diaper according to Modification Example. FIG. 10 is a sectional view in a longitudinal direction of the disposable diaper taken along the line X'3-X3 shown in FIG. 9. An exterior body 1B according to Modification Example has: a foreside exterior topsheet 70F; a rear-side exterior topsheet 70R; a foreside exterior backsheet 80F; a rear-side exterior backsheet 80R; and an exterior center sheet.

The exterior backsheet has: a foreside exterior backsheet 80F which is bonded with the foreside exterior topsheet 70F; and a rear-side exterior backsheet 80R which is bonded with the rear-side exterior backsheet 70R. The exterior center sheet 35 is positioned between a rear end of the foreside exterior topsheet 70F and a front end of the rear-side exterior topsheet 70R in a longitudinal direction, and is positioned between the foreside exterior topsheet 70F and an absorber backsheet 30 and between the rear-side exterior topsheet 70R and the absorber backsheet 30 in a thickness direction.

By providing the exterior center sheet 35, the foreside exterior topsheet 70F and the foreside exterior backsheet 80F can be connected to each other, and the rear-side exterior topsheet 70R and the rear-side exterior backsheet 80R can be connected to each other. Therefore, in a mode in which the exterior topsheet and the exterior backsheet are spaced from each other in the longitudinal direction, exposure of the absorbent main body 1A to the outside can be prevented. Further, in the course of manufacturing, in a state in which the foreside exterior sheet and the rear-side exterior sheet that are spaced from each other are connected to each other, a leg opening unit can be formed, and these exterior sheets can be bonded with the absorbent main body 1A.

Also, the second expanding and contracting unit 52 of the leg-holes elastic member 5R is divided into a plurality of sections at the center in the widthwise direction of the absorber disposition region. Even in the case where the rear leg-holes elastic member 5R is thus divided, since the leg holes elastic member 5R overhang across the end in the widthwise direction of the absorber, it is possible to pull up the rear end of the absorbent main body 1A by the leg opening unit 9 and the rear leg-holes elastic member 5R.

(5) Other Embodiments

As described above, although several embodiments of the present invention are disclosed, the description and drawings forming part of this disclosure are not intended to limit the present invention. From this disclosure, a variety of substitutive embodiments, examples, and operational techniques would become apparent to one ordinarily skilled in the art.

For example, while, in the foregoing embodiments, a pants-type disposable diaper was described by way of example, the present invention is not limited thereto, and may be applied to an open-type disposable diaper, an incontinence pad, and a sanitary napkin or the like.

In so far as an open-type disposable diaper is concerned, for example, in a rear waistline region, an engagingly fitting member such as a fastening tape is provided, and in a front waistline region, a target portion by which the engagingly fitting member is to be hooked is provided.

In addition, the absorbent article may be provided with a central curving unit and a side curving unit, may be provided with at least one of them, or alternatively, may not be provided with the central curving unit and the side curving unit.

Further, although the central curving units and the side curving units of the embodiment are composed of slits formed in the absorber, the structure of the central curving units and the side curving units are not limitative to the slits. The central curving units and the side curving units may be composed of an elastic member which expands and contracts in the longitudinal direction, may be composed of a compression unit by which the absorber is compressed in the thickness direction, or alternatively, may be composed of a low basis weight region which is structured to be lower than the basis weight of the periphery in the absorber. Furthermore, a slit is formed in the absorber, and an elastic member to expand and contract in the longitudinal direction so as to overlap with the slit is provided, whereby a central curving unit and a side curving unit may be composed of the slit and the elastic member.

Also, the crotch elastic member 12 does not always need to be provided. The leg-holes elastic member may not be continuously provided in the widthwise direction, or alternatively, may be discontinuously provided while a part thereof is cut.

In aforementioned embodiments, the absorber 40 has a bi-layered structure of the first absorbent layer 41 and the second absorbent layer 42, but the absorber 40 of the worn article according to further embodiments may be configured from a single layer or may be configured from three or more layers.

As described above, needless to say, the present invention includes various embodiments and the like not described here. Accordingly, the scope of the present invention is defined only by the appended claims in view of the above description. The entire contents of Japanese Patent Application No. 2012-098253 (filed on Apr. 23, 2012) are incorporated in the present specification by reference.

INDUSTRIAL APPLICABILITY

According to the characteristic provided by the present invention, it is possible to provide an absorbent article

REFERENCE SIGNS LIST

1 . . . Disposable diaper (absorbent article)
1A . . . Absorbent main body
1B . . . Exterior body
3 . . . Waist gathers
3A . . . Waist elastic member
4, 4' . . . Front waistline side edge
5 . . . Leg gathers
5F . . . Front leg-holes elastic member
5R . . . Rear leg-holes elastic member
6, 6' . . . Rear waistline side edge
7 . . . Edge part of exterior body
8 . . . waistline opening unit
9 . . . leg opening unit
9C . . . Inclination unit
10 . . . Topsheet
11 . . . joint unit
12 . . . Crotch elastic member
15 . . . Auxiliary sheet
30 . . . Absorber backside sheet
30F . . . Front end
30R . . . Rear end
32 . . . Leakage preventing side sheet
33 . . . Leakage preventing elastic member
35 . . . Nonwoven sheet
40 . . . Absorber
40F . . . Front end
40R . . . Rear end
41 . . . First absorbent layer
41N . . . Concavity portion
42 . . . Second absorbent layer
42FL . . . Front wide part
42N . . . narrow part
42RL . . . Rear wide part
42P . . . Deformation restraining unit
45 . . . Central slit
46 . . . side slit
51 . . . First expanding and contracting unit
52 . . . Second expanding and contracting unit
70F . . . Foreside exterior topsheet
70R . . . Rear-side exterior topsheet
80 . . . Exterior backsheet
80F . . . Foreside exterior backsheet
80R . . . Rear-side exterior backsheet
S1 . . . Front waistline region
S2 . . . Rear waistline region
S3 . . . Crotch region
S31 . . . Front crotch region
S32 . . . Central crotch region
S33 . . . Rear crotch region
L . . . longitudinal direction
IN . . . Inner direction
OUT . . . Outer direction
T . . . Thickness direction
W . . . Widthwise direction

The invention claimed is:

1. An absorbent article having:
a longitudinal direction extending to a body front side and a body rear side of a wearer;
a widthwise direction perpendicular to the longitudinal direction;
an inner direction for facing a wearer;
an outer direction which is opposite to the inner direction;
a crotch region which is adapted to be in contact with a crotch of the wearer;
a front waistline region which is disposed forward of the crotch region, and is adapted to be in contact with a waistline of the wearer;
a rear waistline region which is disposed rearward of the crotch region, and is adapted to be in contact with the waistline of the wearer;
side edges of the front and rear waistline regions are joined together at a joint unit, with the crotch region being located exclusively inwardly of the joint unit in the longitudinal direction;
an absorber which is disposed at least at a center in a widthwise direction of the crotch region;
an exterior body which is positioned at the outer direction side of the absorber, and is disposed on a surface at a non-skin contact side of the absorbent article; and
leg opening units disposed along a leg-line of the wearer and formed in the crotch region, wherein the exterior body has edge parts which form a part of the leg opening units and is positioned outboard of the absorber in a widthwise direction, a rear end of the absorber is positioned in the crotch region, a waistline elastic member exclusively arranged in the rear waistline region that expands and contracts in the widthwise direction in the rear waistline region and a leg-holes elastic member to expand and contract along the leg opening units are disposed at the exterior body in the rear waistline region, the leg-holes elastic member has:
- one pair of first expanding and contracting units which is positioned inside in the longitudinal direction as the first expanding and contracting units go to a center in a widthwise direction, said first expanding and contracting units are positioned outboard of the absorber in the widthwise direction; and
- a second expanding and contracting unit which is positioned in an absorber disposition region in which the absorber is disposed between the first expanding and contracting units, the first expanding and contracting units extend from the outside toward the inside in the front-back direction as they progress from the outside toward the inside in the width direction, edge parts of the exterior body extend across the end of the absorber in the widthwise direction, each edge part extends from the outside toward the inside in the front-back direction as they progress from the outside toward the inside in the width direction, and a crotch elastic member arranged outside of the second expanding and contracting unit in the longitudinal direction that expands and contracts in the widthwise direction is arranged inside of the waistline elastic member in the longitudinal direction and is disposed in the crotch region, wherein an expansion stress of the crotch elastic member is lower than an expansion stress of the leg-holes elastic member and is lower than an expansion stress of the waistline elastic member, the absorber has a rear edge, and the rear edge of the absorber and the crotch elastic member are arranged between the waistline elastic member and the leg-holes elastic member.

2. The absorbent article according to claim 1, wherein at least a part of the second expanding and contracting unit is cut.

3. The absorbent article according to claim 2, wherein an amount of water preservation of the absorber is 300 g or more.

4. The absorbent article according to claim 2, wherein
a side elastic member to respectively contract in a longitudinal direction both ends in the widthwise direction of the absorber is disposed in the crotch region, and
a rear end of the side elastic member and the leg-holes elastic member overlap with each other in a planar view.

5. The absorbent article according to claim 2, wherein a central curving unit that allow the absorber to curve in the inner direction in a convex shape is formed at a center of the crotch region in a widthwise direction.

6. The absorbent article according to claim 2, wherein one pair of side curving units that allow the absorber to curve in outer direction in a convex shape are formed outboard a central curving unit in a widthwise direction in the crotch region.

7. The absorbent article according to claim 1, wherein an amount of water preservation of the absorber is 300 g or more.

8. The absorbent article according to claim 1, wherein
a side elastic member to respectively contract in a longitudinal direction both ends in the widthwise direction of the absorber is disposed in the crotch region, and
a rear end of the side elastic member and the leg-holes elastic member overlap with each other in a planar view.

9. The absorbent article according to claim 1, wherein a central curving unit that allows the absorber to curve in the inner direction in a convex shape is formed at a center of the crotch region in a widthwise direction.

10. The absorbent article according to claim 1, wherein one pair of side curving units that allow the absorber to curve in outer direction in a convex shape are formed outboard of a central curving unit in a widthwise direction in the crotch region.

11. The absorbent article according to claim 1, wherein the length in the widthwise direction of the waist elastic member is longer than the length in the widthwise direction of the crotch elastic member.

12. The absorbent article according to claim 1, wherein the crotch elastic member overlaps the absorbent core in the thickness direction, and the waist elastic member does not overlap the absorbent core.

* * * * *

UNITED STATES PATENT AND TRADEMARK OFFICE
CERTIFICATE OF CORRECTION

PATENT NO. : 10,098,795 B2
APPLICATION NO. : 14/395031
DATED : October 16, 2018
INVENTOR(S) : Hirotomo Mukai et al.

It is certified that error appears in the above-identified patent and that said Letters Patent is hereby corrected as shown below:

In the Specification

In Column 4, Line 62, delete "15 g/m2" and substitute --15 $g/m^2$-- in its place.

In Column 5, Line 13, delete "17 g/m2" and substitute --17 $g/m^2$-- in its place.

In Column 5, Line 27, delete "23 g/m2" and substitute --23 $g/m^2$-- in its place.

In Column 5, Line 41, delete "30 g/m2" and substitute --30 $g/m^2$-- in its place.

In Column 5, Line 47, delete "5 g/m2 and 8 g/m2" and substitute --5 $g/m^2$ and 8 $g/m^2$-- in its place.

In Column 7, Line 1, delete "0.1 g/m2" and substitute --0.1 $g/m^2$-- in its place.

In Column 7, Line 5, delete "15 g/m2" and substitute --15 $g/m^2$-- in its place.

In Column 12, Line 13, delete "500 g/m2" and substitute --500 $g/m^2$-- in its place.

In Column 12, Line 14, delete "500 g/m2" and substitute --500 $g/m^2$-- in its place.

In Column 12, Line 16, delete "260 g/m2" and substitute --260 $g/m^2$-- in its place.

In Column 12, Line 17, delete "g/m2" and substitute --$g/m^2$-- in its place.

Signed and Sealed this
Nineteenth Day of November, 2019

Andrei Iancu
*Director of the United States Patent and Trademark Office*